(12) United States Patent
Chi et al.

(10) Patent No.: US 8,722,885 B1
(45) Date of Patent: May 13, 2014

(54) PHOSPHORESCENT FOUR-COORDINATED PLATINUM (II) COMPLEX

(71) Applicant: National Tsing Hua University, Hsinchu (TW)

(72) Inventors: Yun Chi, Hsinchu (TW); Li-Min Huang, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 14/099,476

(22) Filed: Dec. 6, 2013

(30) Foreign Application Priority Data

Jun. 4, 2013 (TW) .............................. 102119777 A

(51) Int. Cl.
*C07F 15/00* (2006.01)
*C07F 9/547* (2006.01)

(52) U.S. Cl.
USPC ................................................ 546/2; 556/13

(58) Field of Classification Search
USPC ................................................ 546/2; 556/13
See application file for complete search history.

(56) References Cited

U.S. PATENT DOCUMENTS 6,963,005 B2 11/2005 Lecloux et al.
8,288,543 B2 10/2012 Chi et al.

FOREIGN PATENT DOCUMENTS

TW 201037057 A1 10/2010

*Primary Examiner* — Charanjit Aulakh
(74) *Attorney, Agent, or Firm* — Birch, Stewart, Kolasch & Birch, LLP

(57) ABSTRACT

A phosphorescent four-coordinated platinum (II) complex represented by formula (C) is disclosed:

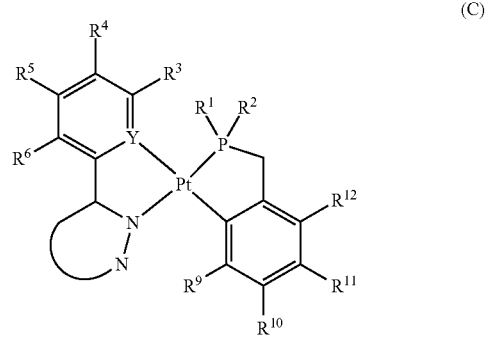

where Y represents N or P; $R^1$, $R^2$, $R^3$, $R^4$, $R^5$, $R^6$, $R^9$, $R^{10}$, $R^{11}$, and $R^{12}$ are the same or different, and independently represent hydrogen, or a substituted or unsubstituted organic group; and

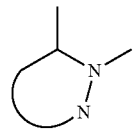 represents

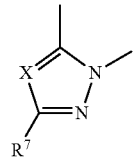

or

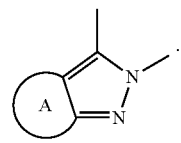

8 Claims, 1 Drawing Sheet

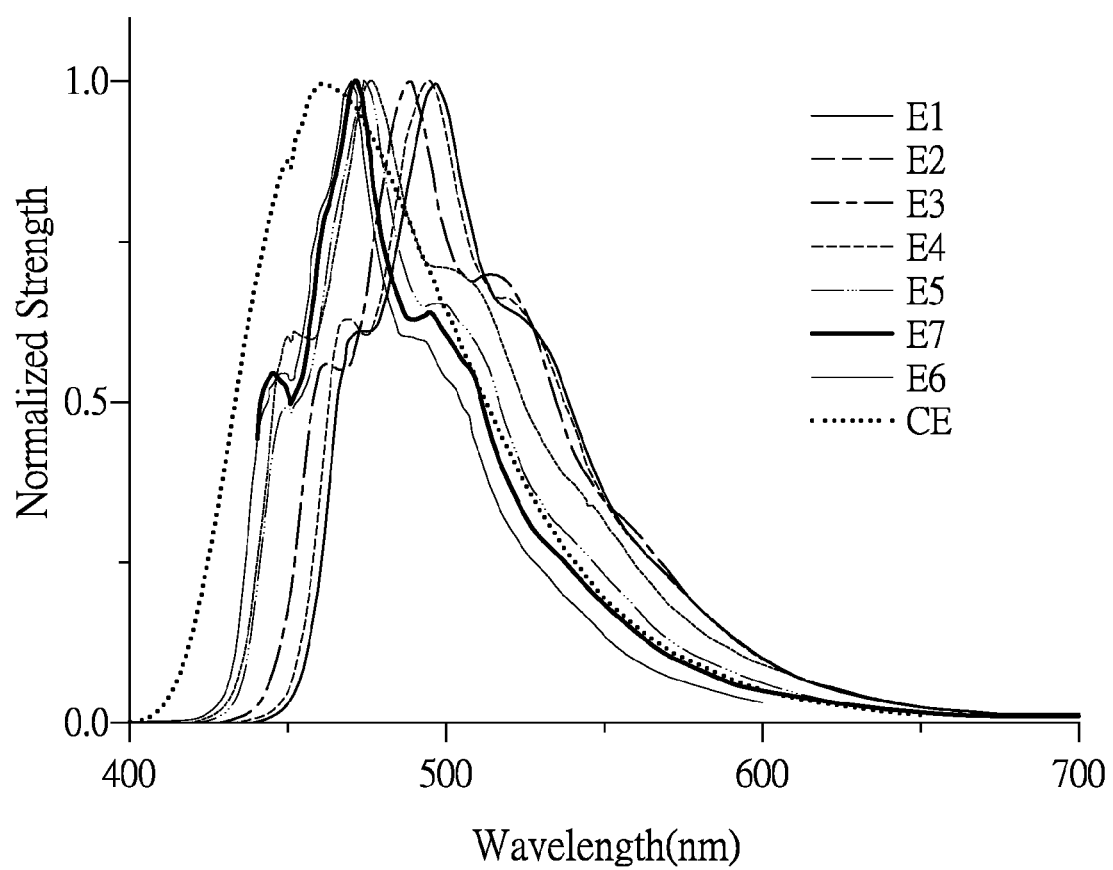

PHOSPHORESCENT FOUR-COORDINATED PLATINUM (II) COMPLEX

CROSS-REFERENCE TO RELATED APPLICATION

This application claims priority of Taiwanese Patent Application No. 102119777, filed on Jun. 4, 2013.

BACKGROUND OF THE INVENTION

1. Field of the Invention

The invention relates to a phosphorescent four-coordinated platinum (II) complex, more particularly to a phosphorescent four-coordinated platinum (II) complex containing two specific monoanionic bidentate ligands chelating with a platinum (II) central metal atom.

2. Description of the Related Art

An organic light emitting diode (hereinafter referred as OLED) needs a material that could be excited to emit a visible light so as to serve as an emitting layer. Conventionally, a compound having an emission peak maximum ranging from 470 nm to 530 nm has inferior blue light emission efficiency.

In general, a phosphorescent four-coordinated platinum (II) complex is used as a blue light emission material for OLED. For example, U.S. Pat. No. 6,963,005 discloses a four-coordinated platinum (II) complex formed by chelating a monoanionic O,O-bidentate ligand and a monoanionic C,P-bidentate ligand with a platinum (II) central atom.

*Inorg. Chem.*, 2007, 11202-11212 discloses a four-coordinated platinum (II) complex that has a maximum quantum yield of 56% in solid state and that is represented by the following formula:

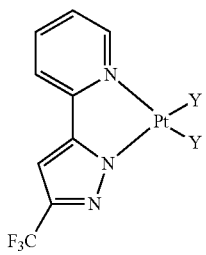

where
Y represents substituted or unsubstituted pyrazolate or chloride substituents.

The thesis of Yao-Te Yen of National Tsing Hua University, 2008, GH000943467 discloses a four-coordinated platinum (II) complex that has a quantum yield of 0% both at room temperature and in dichloromethane solution. The four-coordinated platinum (II) complex is represented by the following formula:

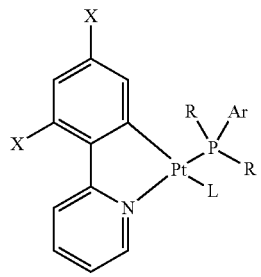

where
X represents hydrogen or fluorine;
Ar represents a fluorine-substituted or unsubstituted phenyl group;
R represents Ar or a methyl group; and
L represents chloride or an isothiocyanato group.

SUMMARY OF THE INVENTION

Therefore, an object of the present invention is to provide a phosphorescent four-coordinated platinum (II) complex that could be excited to emit blue light or blue-green light and that has superior blue light emission quantum yield.

According to the present invention, there is provided a phosphorescent four-coordinated platinum (II) complex represented by formula (C):

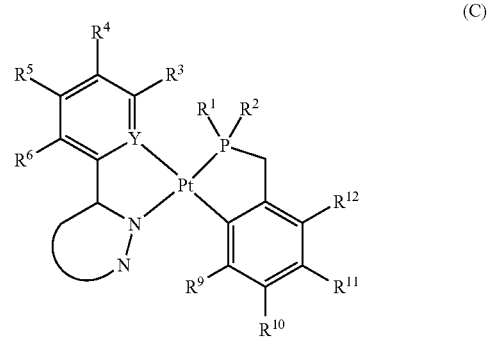

(C)

where
Y represents N or P;
$R^1$, $R^2$, $R^3$, $R^4$, $R^5$, $R^6$, $R^9$, $R^{10}$, $R^{11}$, and $R^{12}$ are the same or different, and independently represent hydrogen, or a substituted or unsubstituted organic group; and

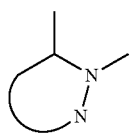

represents

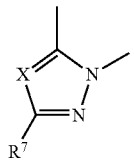

or

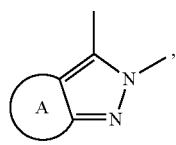

when

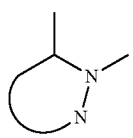

represents

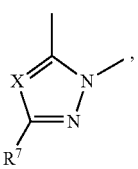

X represents C—R$^8$ or nitrogen; R$^7$ represents a substituted or unsubstituted organic group; and R$^8$ represents hydrogen or a substituted or unsubstituted organic group; and when

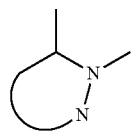

represents

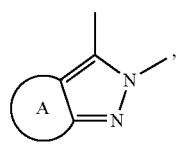

ring A represents a substituted or unsubstituted bridged carbocyclic ring.

Preferably, the phosphorescent four-coordinated platinum (II) complex according this invention includes a platinum (II) central atom, a monoanionic N,N-bidentate ligand (i.e., the monoanionic bidentate ligand

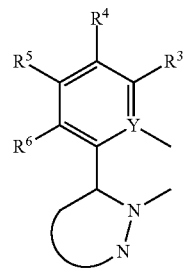

in formula (C) where Y is N) chelating with the platinum (II) central atom, and a monoanionic C,P-bidentate ligand (i.e., the monoanionic bidentate ligand

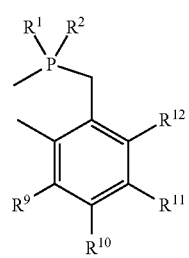

in formula (C)) chelating with the platinum (II) central atom.

When the phosphorescent four-coordinated platinum (II) complex according to this invention is excited, the complex could emit blue light or blue-green light and has superior blue light emission quantum yield.

BRIEF DESCRIPTION OF THE DRAWING

Other features and advantages of the present invention will become apparent in the following detailed description of the preferred embodiment with reference to the accompanying drawing:

FIG. 1 is a visible spectrum that illustrates emission wavelength ranges of complexes E1 to E7 and CE obtained from Examples 1 to 7 and Comparative Example.

DETAILED DESCRIPTION OF THE PREFERRED EMBODIMENTS

A phosphorescent four-coordinated platinum (II) complex according to the present invention is represented by formula (C):

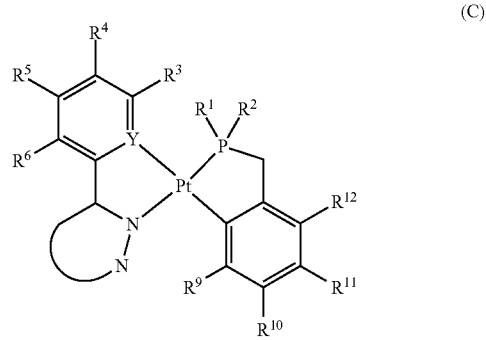

(C)

where
Y represents N or P;
R$^1$, R$^2$, R$^3$, R$^4$, R$^5$, R$^6$, R$^9$, R$^{10}$, R$^{11}$, and R$^{12}$ are the same or different, and independently represent hydrogen, or a substituted or unsubstituted organic group; and

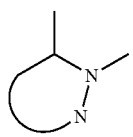

represents

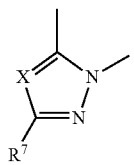

or

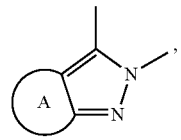

when

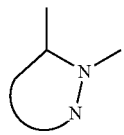

represents

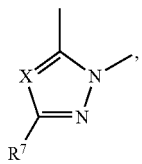

X represents C—$R^8$ or nitrogen; $R^7$ represents a substituted or unsubstituted organic group; and $R^8$ represents hydrogen or a substituted or unsubstituted organic group; and when

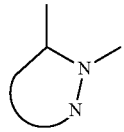

represents

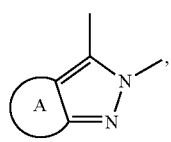

ring A represents a substituted or unsubstituted bridged carbocyclic ring.

The inventors found that in the phosphorescent four-coordinated platinum (II) complex of the present invention, both the monoanionic bidentate ligand

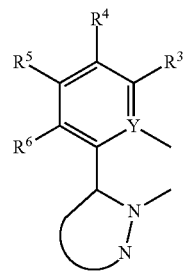

(where Y is N or P, and is preferably N) as a chromophore and the monoanionic bidentate ligand

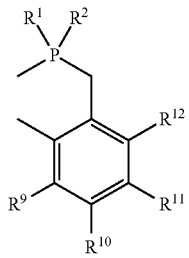

chelate with the platinum (II) central atom so as to regulate an energy gap between the highest occupied molecular orbital (referred as HOMO) and the lowest unoccupied molecular orbital (referred as LUMO) of the phosphorescent four-coordinated platinum (II) complex. Accordingly, the phosphorescent four-coordinated platinum (II) complex of the present invention could emit phosphorescence with an emission peak maximum ranging from 470 nm to 530 nm (i.e., blue light to blue-green light) when the complex is excited.

In addition, the inventors believe that in the phosphorescent four-coordinated platinum (II) complex according to this invention, the benzylphosphino moiety of the monoanionic bidentate ligand

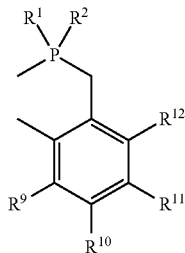

can reduce the molecular stacking between the phosphorescent four-coordinated platinum (II) complexes and can avoid a triplet metal-metal-to-ligand charge transfer transition (referred as $^3$MMLCT) occurred in the common blue-emitting platinum (II) metal complexes. Therefore, the phosphorescent four-coordinated platinum (II) complex according to this invention emits the phosphorescence with significant hypsochromic shift (blue shift) and has good solubility to common organic solvents.

Preferably, Y represents N; $R^1$ and $R^2$ independently represent a substituted or unsubstituted phenyl group; $R^3$, $R^4$, $R^5$, and $R^6$ independently represent hydrogen, a $C_1$-$C_{13}$ alkyl group, or a substituted or unsubstituted aryl group with the proviso that at least one of $R^3$, $R^4$, $R^5$, and $R^6$ is not hydrogen; $R^9$, $R^{10}$, $R^{11}$, and $R^{12}$ independently represent hydrogen, a $C_1$-$C_4$ alkyl group, or a $C_1$-$C_4$ haloalkyl group; $R^7$ represents a $C_4$-$C_{12}$ alkyl group, a $C_1$-$C_4$ haloalkyl group, or a substituted or unsubstituted aryl group; $R^8$ represents hydrogen, a $C_1$-$C_{12}$ alkyl group, a $C_1$-$C_4$ haloalkyl group, or a substituted or unsubstituted aryl group; and the ring A represents a substituted or unsubstituted $C_6$-$C_{10}$ bridged carbocyclic ring.

Preferably, $R^5$ represents a tert-butyl group or a 2,6-diisopropyl phenyl group.

Preferably, $R^7$ represents a tert-butyl group, a trifluoromethyl group, or a 2-trifluoromethyl phenyl group.

Preferably, $R^{10}$ represents hydrogen or a trifluoromethyl group.

Preferably, $R^3$, $R^4$, and $R^6$ represent hydrogen.

Preferably, the phosphorescent four-coordinated platinum (II) complex according to this invention has an emission peak maximum ranging from 470 nm to 530 nm, and more preferably from 470 nm to 500 nm.

The present invention will now be further described by way of the following examples. It is understood that the following examples are used for illustration, and should not be construed as limiting the implementation of the present invention.

Synthesis of Precursor Solution (PS) of Phosphorescent Four-Coordinated Platinum (II) Complex Synthesis Example 1

PS1

Pt(tht)$_2$Cl$_2$ (synthesized according to a method disclosed in *J. Chem. Soc., Dalton Trans.* 1980, 888-894; 100 mg, 1 eq, "tht" represents tetrahydrothiophene), benzyldiphenylphosphine purchased from Alfa Aesar (68 mg, 1.1 eq), and sodium acetate (94 mg, 5 eq) were added in a 50 mL round-bottomed flask, and degassed xylene (purchased from ECHOChemical; Product no: XA2101-000000-72EC; 6 mL) was then added therein with mixing to obtain a mixture, followed by heating to 100° C. and reacting for 12 hours. The mixture was then cooled to room temperature, and a precursor solution (PS1) of a phosphorescent four-coordinated platinum (II) complex was obtained.

Synthesis Example 2

PS2

Pt(tht)$_2$Cl$_2$ (100 mg, 1 eq), diphenyl(4-trifluoromethylbenzyl)phosphine (86 mg, 1.1 eq) synthesized according to a method disclosed in JP 2008-010647, and sodium acetate (94 mg, 5 eq) were added in a 50 mL round-bottomed flask, and degassed xylene (6 ml) was then added therein with mixing to obtain a mixture, followed by heating to 100° C. and reacting for 12 hours. The mixture was then cooled to room temperature, and a precursor solution (PS2) of a phosphorescent four-coordinated platinum (II) complex was obtained.

Synthesis of Phosphorescent Four-Coordinated Platinum (II) Complex

Example 1

E1

3-(4-(tert-butyl)pyridin-2-yl)-7,8,8-trimethyl-4,5,6,7-tetrahydro-2H-4,7-methanoindazole (70 mg, 1 eq) was added into the PS1 obtained from Synthesis Example 1 to obtain a mixture, and the mixture was heated to 100° C. and reacted for 6 hours, followed by cooling to room temperature and removing the solvent. Silica-gel column chromatography was conducted to purify the mixture using an eluent of ethyl acetate (hereinafter referred as EA) and n-hexane (EA:n-hexane=1:3 (by volume)). Recrystallization was then conducted using dichloromethane/n-hexane so as to obtain a white crystalline product, referred to as complex E1 (77.4% yield; 137 mg). The reaction scheme for producing the complex E1 is represented as follows:

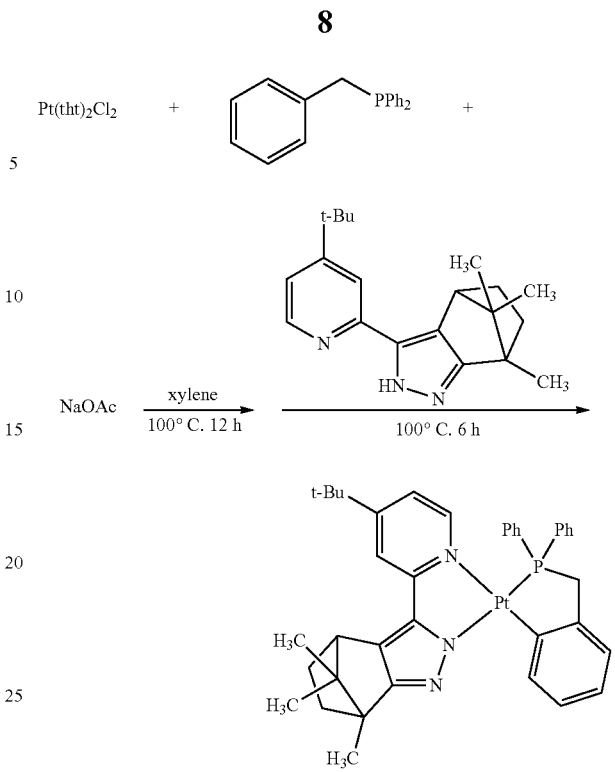

The spectrum analysis for the complex E1 is: $^1$H NMR (400 MHz, CD$_2$Cl$_2$, 298 K) δ 8.97 (d, J=8.1 Hz, 1H), 7.84 (dd, J=10.4, 18.3 Hz, 4H), 7.38-7.51 (m, 8H), 7.06-7.07 (m, 2H), 6.94 (t, J=7.2 Hz, 1H), 6.47 (dd, J=1.8, 6 Hz, 1H), 3.73 (d, J=11.2 Hz, 2H), 2.97 (d, J=3.7 Hz, 1H), 2.08-2.14 (m, 1H), 1.80-1.86 (m, 1H), 1.43-1.47 (m, 1H), 1.41 (s, 3H), 1.25 (s, 9H), 0.97 (s, 3H), 0.84-0.88 (m, 1H), 0.81 (s, 3H) ppm, $^{31}$P NMR (200 MHz, CDCl$_3$, 298 K) δ 36.38 ppm, FAB-MS m/z 779.7 [M+1]$^+$.

Example 2

E2

4-(tert-butyl)-2-(3-(tert-butyl)-1H-pyrazol-5-yl)pyridine (59 mg, 1 eq) was added into the PS1 obtained from Synthesis Example 1 to obtain a mixture, and the mixture was heated to 100° C. and reacted for 6 hours, followed by cooling to room temperature and removing the solvent. Silica-gel column chromatography was conducted to purify the mixture using an eluent of dichloromethane and n-hexane (dichloromethane:hexane=1:1 (by volume)). Recrystallization was then conducted using dichloromethane/n-hexane so as to obtain a light yellow crystalline product, referred to as complex E2 (59.9% yield; 98.9 mg). The reaction scheme for producing the complex E2 is represented as follows:

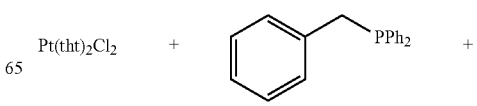

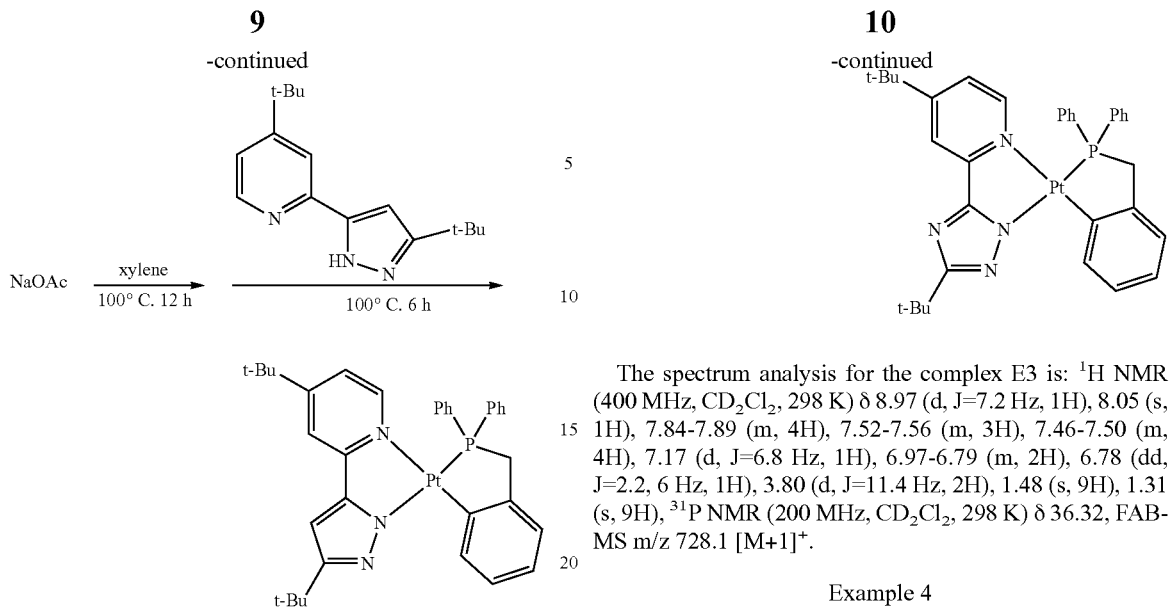

The spectrum analysis for the complex E2 is: ¹H NMR (400 MHz, CD$_2$Cl$_2$, 298 K) δ 9.05 (d, J=7.6 Hz, 1H), 7.86-7.91 (m, 3H), 7.62 (d, J=2.0 Hz, 1H), 7.46-7.54 (m, 5H), 7.26-7.31 (m, 2H), 7.17 (d, J=7.0 Hz, 1H), 6.98-7.11 (m, 4H), 6.60 (s, 1H), 3.80 (d, J=11.4 Hz, 2H), 1.44 (s, 9H), 1.28 (s, 9H) ppm, ³¹P NMR (200 MHz, CD$_2$Cl$_2$, 298 K) δ 36.68 ppm, FAB-MS m/z 727.7 [M+1]⁺.

Example 3

E3

4-(tert-butyl)-2-(3-(tert-butyl)-1H-1,2,4-triaz ol-5-yl)pyridine (59 mg, 1 eq) was added into the PS1 obtained from Synthesis Example 1 to obtain a mixture, and the mixture was heated to 100° C. and reacted for 6 hours, followed by cooling to room temperature and removing the solvent. Silica-gel column chromatography was conducted to purify the mixture using an eluent of EA and n-hexane (EA:n-hexane=1:2 (by volume)). Recrystallization was then conducted using dichloromethane/n-hexane so as to obtain a light yellow crystalline product, referred to as complex E3 (44% yield; 73 mg). The reaction scheme for producing the complex E3 is represented as follows:

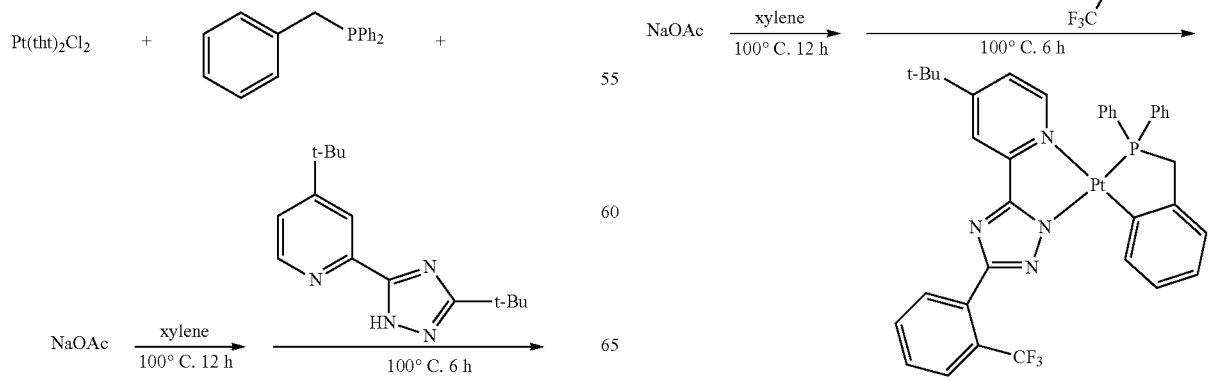

The spectrum analysis for the complex E3 is: ¹H NMR (400 MHz, CD$_2$Cl$_2$, 298 K) δ 8.97 (d, J=7.2 Hz, 1H), 8.05 (s, 1H), 7.84-7.89 (m, 4H), 7.52-7.56 (m, 3H), 7.46-7.50 (m, 4H), 7.17 (d, J=6.8 Hz, 1H), 6.97-6.79 (m, 2H), 6.78 (dd, J=2.2, 6 Hz, 1H), 3.80 (d, J=11.4 Hz, 2H), 1.48 (s, 9H), 1.31 (s, 9H), ³¹P NMR (200 MHz, CD$_2$Cl$_2$, 298 K) δ 36.32, FAB-MS m/z 728.1 [M+1]⁺.

Example 4

E4

4-(tert-butyl)-2-[3-(2-trifluoromethylphenyl)-1 H-1,2,4-triazol-5-yl]pyridine (80 mg, 1 eq) was added into the PS1 obtained from Synthesis Example 1 to obtain a mixture, and the mixture was heated to 100° C. and reacted for 6 hours, followed by cooling to room temperature and removing the solvent. Silica-gel column chromatography was conducted to purify the mixture using an eluent of dichloromethane and n-hexane (dichloromethane:n-hexane=1:3 (by volume)). Recrystallization was then conducted using dichloromethane/n-hexane so as to obtain a white crystalline product, referred to as complex E4 (77.2% yield; 144 mg). The reaction scheme for producing the complex E4 is represented as follows:

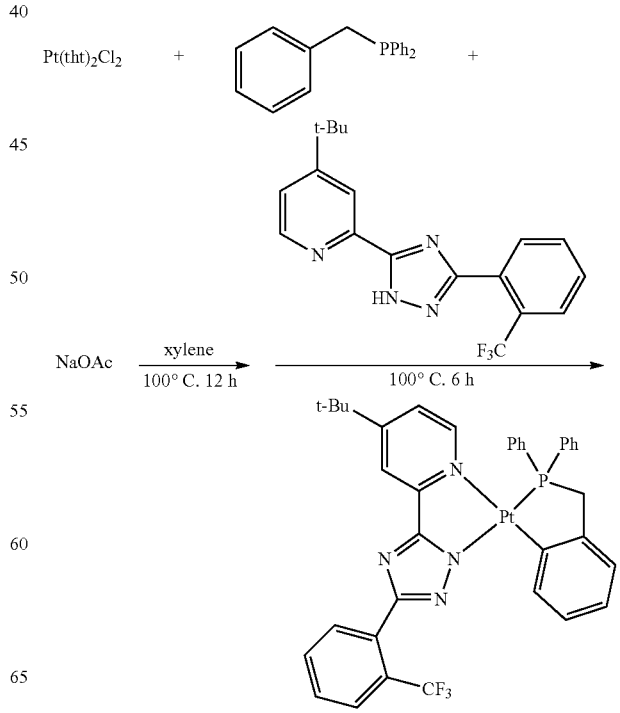

The spectrum analysis for the complex E4 is: $^1$H NMR (400 MHz, CDCl$_3$, 298 K) δ 9.07 (d, J=7.9 Hz, 1H), 8.17 (d, J=2.0 Hz, 1H), 7.99 (d, J=7.7 Hz, 1H), 7.83-7.88 (m, 4H), 7.79 (d, J=7.7 Hz, 1H), 7.56-7.62 (m, 2H), 7.44-7.53 (m, 7H), 7.08-7.15 (m, 2H), 6.99 (t, J=7.1 Hz, 1H), 6.79 (dd, J=2.2, 6 Hz, 1H), 3.80 (d, J=11.4 Hz, 2H), 1.29 (s, 9H), $^{19}$F NMR (400 MHz, CDCl$_3$, 298 K) δ −58.2, $^{31}$P NMR (200 MHz, CDCl$_3$, 298 K) δ 36.35, FAB-MS m/z 815.8 M$^+$.

Example 5

E5

4-(tert-butyl)-2-(3-trifluoromethyl-1H-pyrazol-5-yl)pyridine (61 mg, 1 eq) was added into the PS1 obtained from Synthesis Example 1 to obtain a mixture, and the mixture was heated to 100° C. and reacted for 6 hours, followed by cooling to room temperature and removing the solvent. Silica-gel column chromatography was conducted to purify the mixture using an eluent of dichloromethane and n-hexane (dichloromethane:n-hexane=1:1 (by volume)). Recrystallization was then conducted using dichloromethane/n-hexane so as to obtain a light yellow crystalline product, referred to as complex E5 (60.8% yield; 102 mg). The reaction scheme for producing the complex E5 is represented as follows:

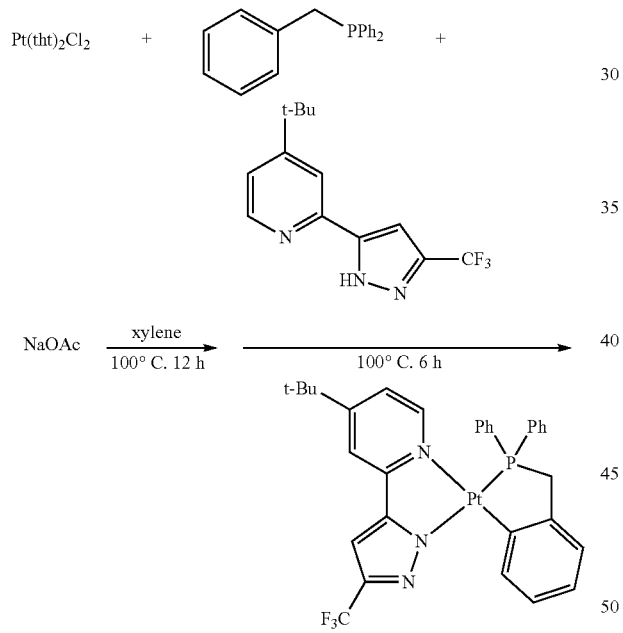

The spectrum analysis for the complex E5 is: $^1$H NMR (400 MHz, CDCl$_3$, 298 K) δ 8.89 (d, J=8.3 Hz, 1H), 7.83 (dd, J=8.1, 11.7 Hz, 4H), 7.61 (d, J=1.4 Hz, 1H), 7.56 (d, J=6.1 Hz, 1H), 7.42-7.51 (m, 6H), 7.11 (t, J=6.4 Hz, 2H), 6.98 (t, J=7.4 Hz, 1H), 6.94 (s, 1H), 6.64 (dd, J=2.1, 6.1 Hz, 1H), 3.77 (d, J=11.4 Hz, 2H), 1.26 (s, 9H), $^{19}$F NMR (400 MHz, CDCl$_3$, 298 K) δ −60.7, $^{31}$P NMR (200 MHz, CDCl$_3$, 298 K) δ 36.24, FAB-MS m/z 738.7 M$^+$.

Example 6

E6

4-(2,6-diisopropylphenyl)-2-(3-trifluoromethyl-1H-pyrazol-5-yl)pyridine (84 mg, 1 eq) was added into the PS1 obtained from Synthesis Example 1 to obtain a mixture, and the mixture was heated to 100° C. and reacted for 6 hours, followed by cooling to room temperature and removing the solvent. Silica-gel column chromatography was conducted to purify the mixture using an eluent of dichloromethane and n-hexane (dichloromethane:n-hexane 1:1). Recrystallization was then conducted using dichloromethane/n-hexane so as to obtain a light yellow crystalline product, referred to as complex E6 (44.3% yield; 85 mg). The reaction scheme for producing the complex E6 is represented as follows:

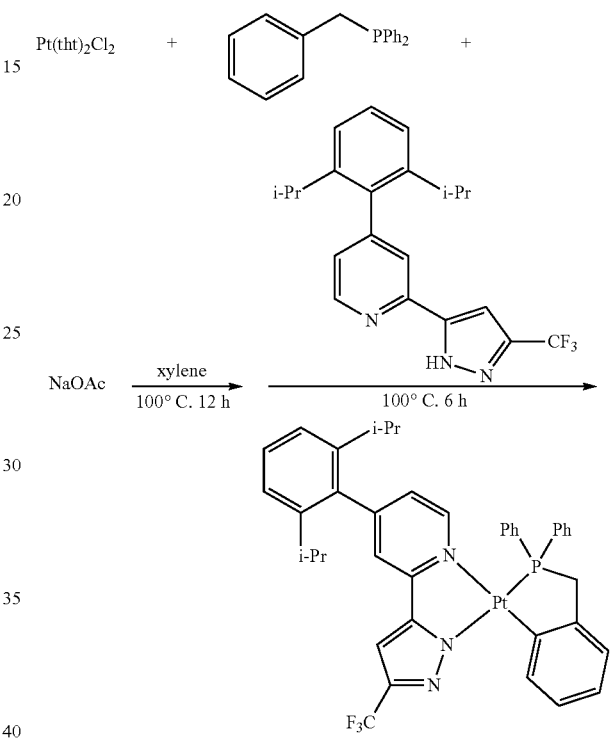

The spectrum analysis for the complex E6 is: $^1$H NMR (400 MHz, CDCl$_3$, 298 K) δ 8.85 (d, J=8.3 Hz, 1H), 7.85-7.90 (m, 4H), 7.63 (d, J=5.7 Hz, 1H), 7.42-7.51 (m, 7H), 7.35 (t, J=7.8 Hz, 1H), 7.18 (d, J=7.8 Hz, 2H), 7.13-7.16 (m, 2H), 7.00 (t, J=7.4 Hz, 1H), 6.88 (s, 1H), 6.47 (dd, J=1.7, 5.7 Hz, 1H), 3.82 (d, J=11.4 Hz, 2H), 2.41 (hept, J=6.8 Hz, 2H), 1.10 (d, J=6.8 Hz, 6H), 0.99 (d, J=6.8 Hz, 6H), $^{19}$F NMR (400 MHz, CDCl$_3$, 298 K) δ −60.7, $^{31}$P NMR (200 MHz, CDCl$_3$, 298 K) δ 36.81, FAB-MS m/z 842.9 M$^+$.

Example 7

E7

4-(tert-butyl)-2-(3-trifluoromethyl-1H-pyrazol-5-yl)pyridine (61 mg, 1 eq) was added into the PS2 obtained from Synthesis Example 2 to obtain a mixture, and the mixture was heated to 100° C. and reacted for 6 hours, followed by cooling to room temperature and removing the solvent. Silica-gel column chromatography was conducted to purify the mixture using an eluent of dichloromethane and n-hexane (dichloromethane:n-hexane=1:1). Recrystallization was then conducted using dichloromethane/n-hexane so as to obtain a light yellow crystalline product, referred to as complex E7 (63.5% yield; 107 mg). The reaction scheme for producing the complex E7 is represented as follows:

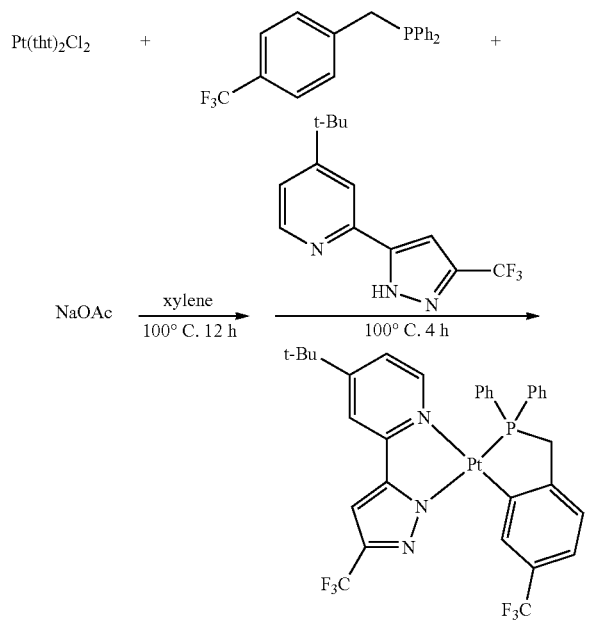

The spectrum analysis for the complex E7 is: $^1$H NMR (400 MHz, CDCl$_3$, 298 K) δ 9.38 (s, 1H), 7.80-7.85 (m, 4H), 7.62 (s, 1H), 7.50-7.55 (m, 3H), 7.44-7.48 (m, 4H), 7.17-7.21 (m, 2H), 6.95 (s, 1H), 6.66 (dd, J=2.1, 6.1 Hz, 1H), 3.77 (d, J=11.5 Hz, 2H), 1.27 (s, 9H), $^{19}$F NMR (400 MHz, CDCl$_3$, 298 K) δ −61.17 (s, 3F), −62.17 (s, 3F).

Comparative Example

CE

The four-coordinated platinum (II) complex CE of Comparative Example was made according to the Example 1 disclosed in U.S. Pat. No. 6,963,005B2. The reaction scheme for producing the complex CE is represented as follows:

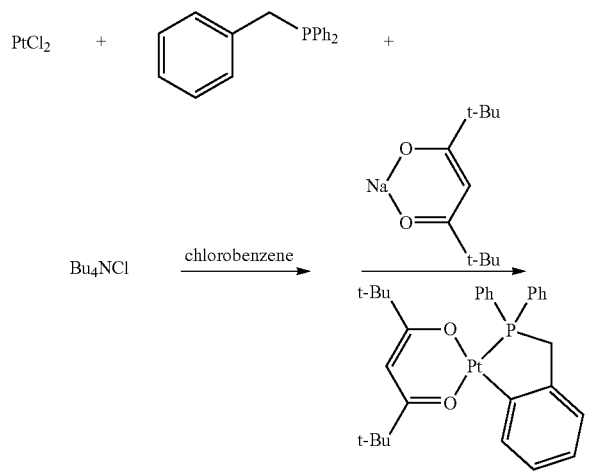

[The Emission Peak Maximum and Quantum Yield]

Each of the complexes E1 to E7 and CE obtained from Examples 1 to 7 and Comparative Example was subjected to a detection process to detect a visible emission spectrum and its emission peak maximum at room temperature (298 K) using a fluorescence spectrometer (purchased from Edinburgh Instruments; Model no.: FL928P), and the resultant data are shown in FIG. 1 and Table 1. The quantum yield at solid state was measured using an integrating sphere (purchased from Edinburgh Instruments), and the resultant data are shown in Table 1.

TABLE 1

| Complex | E1 | E2 | E3 | E4 | E5 | E6 | E7 | CE |
|---|---|---|---|---|---|---|---|---|
| Excitation Wavelength (nm) | 420 | 390 | 350 | 380 | 390 | 360 | 370 | 360 |
| Emission peak Maximum (nm) | 496 | 495 | 488 | 477 | 474 | 470 | 472 | 460 |
| Quantum Yield (%) | 76.6 | 71.2 | 74.9 | 91.9 | 89.8 | 80.8 | 100 | 56 |

As shown in FIG. 1 and Table 1, the complexes E1 to E7 obtained from Examples 1 to 7 of the present invention have the emission peak maxima ranging from 470 nm to 496 nm, which demonstrates that the complexes E1 to E7 emit blue light to blue-green light when they are excited. Additionally, the complexes E1 to E7 have the blue light emission quantum yield ranging from 71.2% to 100%. The blue light emission quantum yield of the complex CE is 56%. Therefore, the blue light emission quantum yield of the complexes E1 to E7 is about 27-78% higher than that of the complex CE.

To sum up, when the phosphorescent four-coordinated platinum (II) complexes according to this invention are excited, the complexes could emit blue light to blue-green light and have superior blue light emission quantum yield ranging from 71.2% to 100%. The abovementioned complexes are suitable for use in blue light and white light phosphorescent OLED.

While the present invention has been described in connection with what are considered the most practical and preferred embodiments, it is understood that this invention is not limited to the disclosed embodiments but is intended to cover various arrangements within the spirit and scope of the broadest interpretation so as to encompass all such modifications and equivalent arrangements.

What is claimed is:

1. A phosphorescent four-coordinated platinum (II) complex represented by formula (C):

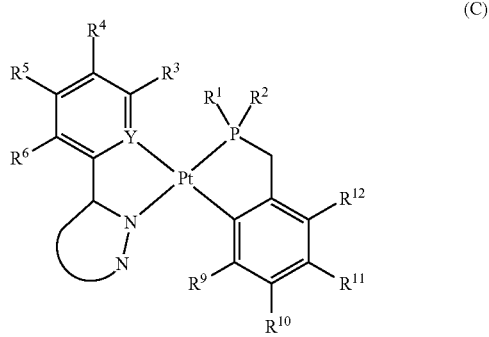

(C)

where
Y represents N or P;
$R^1$, $R^2$, $R^3$, $R^4$, $R^5$, $R^6$, $R^9$, $R^{10}$, $R^{11}$, and $R^{12}$ are the same or different, and independently represent hydrogen, or a substituted or unsubstituted organic group; and represents

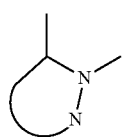

or

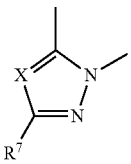

when

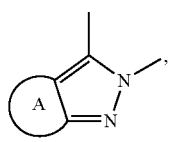

represents

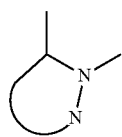

X represents C—R⁸ or nitrogen; $R^7$ represents a substituted or unsubstituted organic group; and $R^8$ represents hydrogen or a substituted or unsubstituted organic group; and
when

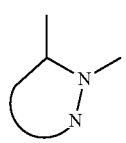

represents

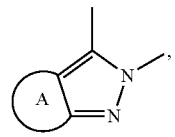

ring A represents a substituted or unsubstituted bridged carbocyclic ring.

2. The phosphorescent four-coordinated platinum (II) complex according to claim 1, wherein:

Y represents N;

$R^1$ and $R^2$ independently represent a substituted or unsubstituted phenyl group;

$R^3$, $R^4$, $R^5$, and $R^6$ independently represent hydrogen, a $C_1$-$C_{13}$ alkyl group, or a substituted or unsubstituted aryl group with the proviso that at least one of $R^3$, $R^4$, $R^5$, and $R^6$ is not hydrogen;

$R^9$, $R^{10}$, $R^{11}$, and $R^{12}$ independently represent hydrogen, a $C_1$-$C_4$ alkyl group, or a $C_1$-$C_4$ haloalkyl group;

$R^7$ represents a $C_4$-$C_{12}$ alkyl group, a $C_1$-$C_4$ haloalkyl group, or a substituted or unsubstituted aryl group;

$R^8$ represents hydrogen, a $C_1$-$C_{12}$ alkyl group, a $C_1$-$C_4$ haloalkyl group, or a substituted or unsubstituted aryl group; and said ring A represents a substituted or unsubstituted $C_6$-$C_{10}$ bridged carbocyclic ring.

3. The phosphorescent four-coordinated platinum (II) complex according to claim 2, wherein $R^5$ represents a tert-butyl group or a 2,6-diisopropyl phenyl group.

4. The phosphorescent four-coordinated platinum (II) complex according to claim 2, wherein $R^7$ represents a tert-butyl group, a trifluoromethyl group, or a 2-trifluoromethyl phenyl group.

5. The phosphorescent four-coordinated platinum (II) complex according to claim 2, wherein $R^{10}$ represents hydrogen or a trifluoromethyl group.

6. The phosphorescent four-coordinated platinum (II) complex according to claim 2, wherein $R^3$, $R^4$, and $R^6$ represent hydrogen.

7. The phosphorescent four-coordinated platinum (II) complex according to claim 1, which has an emission peak maximum ranging from 470 nm to 530 nm.

8. The phosphorescent four-coordinated platinum (II) complex according to claim 7, wherein said emission peak maxima ranges from 470 nm to 500 nm.

* * * * *